(12) United States Patent
Dani

(10) Patent No.: US 8,404,230 B2
(45) Date of Patent: Mar. 26, 2013

(54) THERAPEUTIC COMBINATION COMPRISING A PULMONARY SURFACTANT AND ANTIOXIDANT ENZYMES

(75) Inventor: Carlo Dani, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/402,148

(22) Filed: Feb. 22, 2012

(65) Prior Publication Data

US 2012/0148554 A1 Jun. 14, 2012

Related U.S. Application Data

(62) Division of application No. 12/877,468, filed on Sep. 8, 2010.

(30) Foreign Application Priority Data

Sep. 8, 2009 (EP) .................................... 09169719

(51) Int. Cl.
*A61K 38/54* (2006.01)
*A61K 38/43* (2006.01)

(52) U.S. Cl. ..................................... 424/94.2; 424/94.1

(58) Field of Classification Search ........................ None
See application file for complete search history.

(56) References Cited

U.S. PATENT DOCUMENTS 5,264,211 A 11/1993 Gonenne

OTHER PUBLICATIONS

Walther et al. American J. Phys. Lung Physiol. 1995 269; 5: L613-L617.*
European Search Report in Application 09169719.3, issued Feb. 23, 2010.
Jonathan M. Davis, et al.; "Safety and Pharmacokinetics of Multiple Doses of Recombinant Human CuZn Superoxide Dismutase Administered Intratracheally to Premature Neonates With Respiratory Distress Syndrome"; XP009129085; Pediatrics; vol. 100; No. 1 Jul. 1997; pp. 24-30.
R. Skelton, et al.; "Bronchopulmonary dysplasia: prevention, management and long-term outlook"; Current Paediatrics, (1996), vol. 6, pp. 119-124.
Carlo Dani, et al.; "Superoxide Dismutase and Catalase Activity in Naturally Derived Commercial Surfactants"; Pediatric Pulmonology; XP009129065; 2009; vol. 44; pp. 1125-1131.
Glynn A. B. Russell; "Antioxidants and neonatal lung disease"; XP009129064; Eur J. Pediatr; 1994; 153 [Suppl 2] pp. S36-S41.
Jonathan M. Davis, et al.; "Pharmacologic Interactions of Exogenous Lung Surfactant and Recombinant Human Cu/Zn Superoxide Dismutase"; XP009129083; Pediatric Research; vol. 35; No. 1; 1994; pp. 37-40.
Frans J. Walther, et al.; "Prevention of Oxygen Toxicity with Superoxide Dismutase and Catalase in Premature Lambs"; Journal of Free Radicals in Biology & Medicine; 1986; vol. 2; pp. 289-293.
Walti et al. (Effects of Exogenous Surfactant and Recombinant Human Copper-Zinc Superoxide Dismutase on Oxygen-Dependent Antimicrobial Defenses. Biology of the Neonate 2002; 2: 96 102)
Barnard et al. (Mitigation of oxidant injury to lung microvasculature by intratracheal instillation of antioxidant enzymes. American J. Phys. 1993 265(4) L340-L345).
Barnard et al. (Mitigation of oxidant injury to lung microvasculature by intratracheal instillation of antioxidant enzymes. American J. Phys. 1993 265(4) L340-L345).
Ramanthan et al. (A randomized, Multicenter Masked Comparison Trial of Poractant Alfa (Curosurf) versus Beractant (Survanta) in the Treatment of Respiratory Distress Syndrome in Preterm Infants. American J Perinatology (2004) 21(3): 109-119).
Steinhorn et al. (Liquid Ventilation Attenuates Pulmonary Oxidative Damage. Journal of Critical Care, 1999 14(1) 20-28).
M. L. Barnard et al., Am. J. of Physiol Lung Cellular and Molecular Physiology, vol. 265, pp. L340-L345 (1993).

* cited by examiner

*Primary Examiner* — Chris R Tate
*Assistant Examiner* — Douglas F White
(74) *Attorney, Agent, or Firm* — Oblon, Spivak, McClelland, Maier & Neustadt, L.L.P.

(57) ABSTRACT

Administration of an exogenous pulmonary surfactant in combination with antioxidant enzymes is effective for the prevention of bronchopulmonary dysplasia (BPD) and decreases the markers of pulmonary oxidative stress.

11 Claims, 3 Drawing Sheets

US 8,404,230 B2

THERAPEUTIC COMBINATION COMPRISING A PULMONARY SURFACTANT AND ANTIOXIDANT ENZYMES

CROSS REFERENCES TO RELATED APPLICATIONS

This application is a Divisional Application of U.S. patent application Ser. No. 12/877,468, filed on Sep. 8, 2010, and claims priority to European Patent Application No. 09169719.3, filed on Sep. 9, 2009.

BACKGROUND OF THE INVENTION

1. Field of the Invention

The present invention relates to compositions for the treatment of preterm infants. The present invention also relates to methods for reducing the pulmonary oxidative damages and the risk of developing bronchopulmonary dysplasia in preterm infants.

2. Discussion of the Background

The human lung consists of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

The lung surfactant complex is primarily composed of lipid and contains minor amounts of various proteins. An absence of adequate levels of this complex results in malfunction of the lungs. This syndrome is called Respiratory Distress Syndrome (RDS), and it commonly affects preterm infants.

The mainstay of the treatment of RDS is the replacement therapy with exogenous pulmonary surfactant preparations. Exogenous pulmonary surfactants are currently administered by endotracheal instillation as a suspension in a saline aqueous solution to intubated pre-term infants kept under mechanical ventilation with oxygen.

Although said therapy has greatly increased postnatal survival, children surviving RDS have a high risk of developing bronchopulmonary dysplasia (BPD), a complication impairing lung development and ultimately leading to impaired breathing. Evidence indicates oxidative injuries of lung tissues play an important role in the pathogenesis of BPD and that the reduced antioxidant enzymes activities during hyperoxia result in increased susceptibility to bronchopulmonary dysplasia.

To counteract the effects of reactive oxygen species, it has been proposed to supplement surfactant preparations with antioxidant enzymes, such as superoxide dismutase and catalase, which are often deficient in the premature lung. However, so far, no indications have been provided regarding the therapeutically effective dose of said enzymes in humans without altering the surface activity of the surfactant or causing other side effects. For instance, it has been reported that scavenging of reactive oxygen species by superoxide dismutase may compromise the phagocytic bactericidal activity.

There is therefore still a need to develop a safe medicament effectively reducing the markers of oxidative stress, and hence the risk of BPD in infants suffering from RDS.

SUMMARY OF THE INVENTION

Accordingly, it is one object of the present invention to provide novel compositions for the treatment of preterm infants.

It is another object of the present invention to provide novel methods for reducing the pulmonary oxidative damages and the risk of developing bronchopulmonary dysplasia in preterm infants.

These and other objects, which will become apparent during the following detailed description, have been achieved by the inventors' discovery that an exogenous pulmonary surfactant in combination with CuZn superoxide dismutase at a unit dose of from 2000 to 10000 U/kg and catalase at a unit dose of from 2000 to 4000 U/kg for use for the prevention of bronchopulmonary dysplasia (BPD) is effective.

Preferably the exogenous pulmonary surfactant is a modified natural pulmonary surfactant. The preferred modified natural pulmonary surfactant is poractant alfa, more preferably administered at a unit dose from 100 to 200 mg/kg.

In a second aspect, the invention provides a combination of:

(a) an exogenous pulmonary surfactant; and (b) CuZn superoxide dismutase at a unit dose from 2000 to 10000 U/kg; and catalase at a unit dose of from 2000 to 4000 U/kg, for simultaneous, sequential or separate administration for the prevention of bronchopulmonary dysplasia (BPD), preferably for simultaneous administration.

In a third aspect, the invention provides a medicament comprising a fixed combination of an exogenous pulmonary surfactant with CuZn superoxide dismutase at a unit dose of from 2000 to 10000 U/kg and catalase at a unit dose of from 2000 to 4000 U/kg.

Said medicament is advantageously in a form suitable for inhalation or intratracheal administration.

In a fourth aspect, the invention provides a kit comprising:

(a) an exogenous pulmonary surfactant and a pharmaceutically acceptable carrier or diluent in a first unit dosage form;

(b) CuZn superoxide dismutase at a unit dose of from 2000 to 10000 U/kg, and optionally a pharmaceutically acceptable carrier or diluent in a second unit dosage form;

(c) catalase at a unit dose of from 2000 to 4000 U/kg, and optionally a pharmaceutically acceptable carrier or diluent in a third unit dosage form; and (d) container means for containing said first, second and third dosage forms.

According to a particular aspect, superoxide dismutase and catalase may be present in a single dosage form, with optionally a pharmaceutically acceptable carrier or diluent.

In a fifth aspect, the invention provides the use of an exogenous pulmonary surfactant in combination with CuZn superoxide dismutase at a unit dose of from 2000 to 10000 U/kg and catalase at a unit dose of from 2000 to 4000 U/kg for the preparation of a medicament for the prevention of bronchopulmonary dysplasia (BPD).

In a sixth aspect, the invention provides a method for the prevention of bronchopulmonary dysplasia, by administering to a patient in need thereof an exogenous pulmonary surfactant in combination with CuZn superoxide dismutase at a unit dose of from 2000 to 10000 U/kg and catalase at a unit dose of from 2000 to 4000 U/kg.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
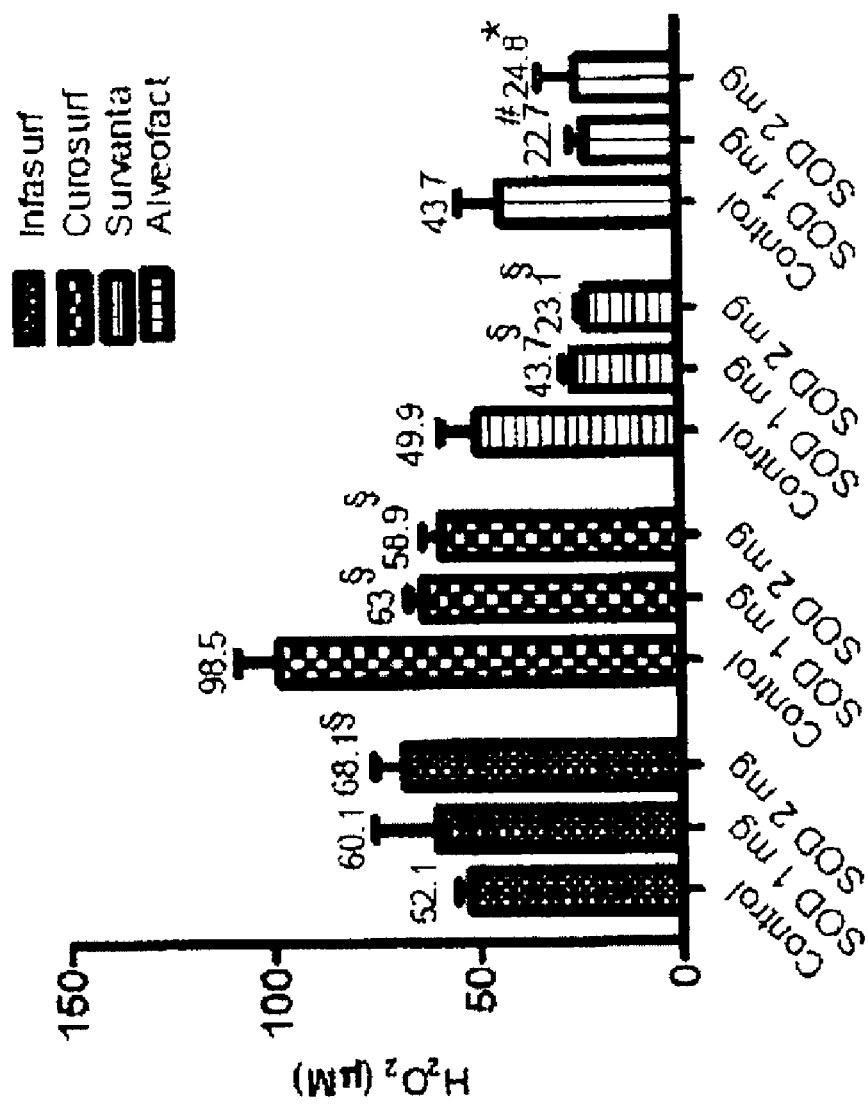
FIG. 1 shows the $H_2O_2$ concentration in the four studied modified natural pulmonary surfactants after the addition of 100 mM of $H_2O_2$ (control) and 1 or 2 mg of superoxide dismutase (SOD). Mean values and SDs. *p<0.05 vs. control; # p<0.005 vs. control; §p<0.0001 vs. control. Data are the difference between the time 0 and end experiment $H_2O_2$ concentration.

The term "antioxidant enzymes" refers to enzymes catalyzing the dismutation of superoxide, one of the main reactive oxygen species in the cell, into oxygen and hydrogen peroxide.

"CuZn superoxide dismutase" means a protein having an amino acid sequence identical, or substantially identical, to the amino acid sequence of a naturally-occurring CuZn superoxide dismutase, whether of human, bovine or other mammalian origin, and having the biological activity of such naturally-occurring CuZn superoxide dismutase.

"Catalase" means a protein having an amino acid sequence identical, or substantially identical, to the amino acid sequence of a naturally-occurring catalase, whether of human, bovine or other mammalian origin, and having the biological activity of such naturally-occurring catalase.

For "unit dose" it is meant is the amount of the surfactant or the enzyme administered to a patient in a single dose.

For the enzymes, the doses are expressed as U per kg of body weight.

One U is defined as the amount of the enzyme that catalyzes the conversion of 1 micromole of substrate per minute.

Since the body weight of preterm infants ranges from about 500 grams to 1500 grams, the unit dose can be calculated accordingly.

For instance, a unit dose of CuZn superoxide dismutase ranging from 2000 to 10000 U/kg corresponds to a range of about 1000 to 15000 U, while a unit dose of catalase ranging from 2000 to 4000 U/kg corresponds to a range of about 1000 to 6000 U.

The term "bronchopulmonary dysplasia (BPD)" refers to a chronic pulmonary disorder, also known as chronic lung disease (CLD) that is the consequence of unresolved or abnormally repaired lung damage.

BPD typically occurs in very low birth weight (VLBW) infants who sustain lung damage as a result of oxygen toxicity and barotrauma from mechanical ventilation early in life.

The term "exogenous pulmonary surfactant" refers to compositions mimic that of the endogenous pulmonary surfactant useful for the prevention and/or treatment of diseases related to surfactant deficiency or dysfunction According to Wilson D (*Expert Opin. Pharmacother.*, 2001, 2(9), 1479-1493, which is incorporated herein by reference in its entirety), exogenous pulmonary surfactants can be classified in four different types:

i) "natural" surfactants which are those recovered intact from lungs or amniotic fluid without extraction and have the lipid and protein composition of natural, endogenous, surfactant. They carry a potential infection risk because they cannot be sterilized, as heat denatures the hydrophilic proteins SP-A and SP-D. These surfactants are not available commercially;

ii) "modified natural" surfactants which are lipid extracts of minced mammalian lung or lung lavage. Due to the lipid extraction process used in the manufacture process, the hydrophilic proteins SP-A and SP-D are lost. These preparations have variable amounts of SP-B and SP-C and, depending on the method of extraction, may contain non-surfactant lipids, proteins or other components. Some of the modified natural surfactants present on the market, like Survanta (vide ultra) are spiked with synthetic components such as tripalmitin, dipalmitoylphosphatidylcholine and palmitic acid.

iii) "artificial" surfactants which are simply mixtures of synthetic compounds, primarily phospholipids and other lipids that are formulated to mimic the lipid composition and behaviour of natural surfactant. They are devoid of surfactant apoproteins;

iv) "reconstituted" surfactants which are artificial surfactants to which have been added surfactant proteins/peptides isolated from animals or proteins/peptides manufactured through recombinant technology such as those described in WO 95/32992, or synthetic surfactant protein analogues such as those described in WO 89/06657, WO 92/22315 and WO 00/47623, all of which are incorporated herein by reference in their entireties.

The term "Poractant alfa" refers to a modified natural surfactant extracted from porcine lungs substantially consisting of polar lipids, mainly phospholipids and the proteins, SP-B and SP-C. Poractant alfa is available under the trademark CUROSURF®.

The term "fixed combination" means a combination wherein the active substances are in a fixed quantitative ratio.

"Pharmaceutical acceptable" refers to a medium that do no not produce an allergic or similar untoward reaction when administered to an infant.

"Surfactant activity" for a pulmonary surfactant preparation is defined as the ability to lower the surface tension.

The in vitro efficacy of exogenous surfactant preparations is commonly tested by measuring its capability of lowering the surface tension using suitable apparatus such as Wilhelmy Balance, Pulsating Bubble Surfactometer, Captive Bubble Surfactometer, or Capillary Surfactometer.

The in vivo efficacy of exogenous surfactant preparations is tested by measuring lung mechanics in pre-term animal models according to known methods.

The term "severe RDS" indicates a form of infant respiratory distress syndrome inversely related to the gestional age and/or birth weight which can be diagnosed clinically and/or radiographically according to known methods.

The term "synergistic" means that the activity of the two compounds is more than would be expected by summing their respective individual activities in a given assay.

The present invention is based on the unexpected finding that CuZn superoxide dismutase and catalase, at certain doses, act synergistically on the scavenger activity towards reactive oxygen species of exogenous pulmonary surfactants. Therefore, the present invention is directed to an exogenous pulmonary surfactant in combination with CuZn superoxide dismutase at a unit dose of from 2000 to 10000 U/kg and catalase at a unit dose of from 2000 to 4000 U/kg for use for the prevention of bronchopulmonary dysplasia (BPD).

The present invention also provides an exogenous pulmonary surfactant in combination with CuZn superoxide dismutase at a unit dose of from 2000 to 10000 U/kg and catalase at a unit dose of from 2000 to 4000 U/kg for use for reducing the risk of developing bronchopulmonary dysplasia (BPD).

Contrary to the prior art, the use of said antioxidant enzymes at the claimed unit doses does not inactivate the modified natural pulmonary surfactant.

Moreover, the use of a combination of enzymes permits an increase of the scavenger activity of all the surfactants, while, as shown in Example 1, the effect of the addition of single enzymes appears to be dependent on their composition.

Any exogenous pulmonary surfactant may be suitable for use in the present invention. Advantageously the exogenous pulmonary surfactant is selected from the group of modified natural pulmonary surfactants, artificial surfactants and reconstituted surfactants. More advantageously, modified natural pulmonary surfactants currently available for treating respiratory distress system and other pulmonary conditions may be used. These include, but are not limited to, bovine lipid surfactant BLES® (BLES Biochemicals, Inc. London, Ont), calfactant (Infasurf®, ONY, Inc. Amherst, N.Y., USA), bovactant (Alveofact®, Boehringer Ingelheim Pharma, inghelheim, Germany), Surfactant TA (Surfacten®, Tokyo Tanabe, Japan), poractant alfa (Curosurf®, Chiesi Farmaceutici SpA, Parma, Italy), beractant (Survanta®, Abbott Laboratories, Inc., Abbott Park, Ill.). Preferably, the modified natural pulmonary surfactant is poractant alfa.

Advantageously, the surfactant unit dose ranges of from about 20 mg/kg to about 300 mg/kg, preferably from 80 to 200 mg/kg.

It being understood, of course, that the exact dose of surfactant will depend upon factors such as the route of administration, the age and condition of the patient, the severity of the condition being treated, and other factors known to the skilled practitioner.

According to the preferred embodiment of the invention, poractant alfa is administered at a unit dose from 100 to 200 mg/kg.

The antioxidant enzymes CuZn superoxide dismutase and catalase may be of different origin and are commercially available, for example from Sigma Chemical Co., St Luis, Mo., USA.

Otherwise, they may be prepared by recombinant techniques according to known methods.

Advantageously, human CuZn superoxide dismutase is used, at a dose of from 2000 to 10000 U/kg, preferably from 2500 to 8000 U/kg, more preferably from 2500 to 6000 U/kg.

Human CuZn superoxide dismutase from erythrocyte or liver, or human recombinant CuZn superoxide dismutase are preferably used.

Human catalase is advantageously used, administered at a dose of from 2000 to 4000 U/kg, preferably from 2500 to 3500 U/kg, more preferably of 3000 U/kg.

Human catalase from erythrocyte or liver, or human recombinant catalase is preferably used.

Given the assay of the enzymes, the skilled person can determine the correspondence between the specific activity expressed in U and mg of protein (enzyme).

The combination of the exogenous pulmonary surfactant with CuZn superoxide dismutase and catalase at the claimed doses may be administered sequentially, separately or together.

Advantageously, when the three components are administered together, they are administered as a fixed combination.

Therefore, the present invention also concerns a medicament comprising said three active components as a fixed combination in form of pharmaceutical composition, e.g. in the form of solutions, dispersions, suspensions or dry powders. Preferably, said compositions comprise the claimed combination suspended in a suitable physiologically tolerable solvent.

More preferably, the formulation comprises an aqueous solution, preferably sterile, which may also comprise pH buffering agents and other pharmaceutically acceptable excipients such as polysorbate 20, polysorbate 80 or sorbitan monolaurate as wetting agents and sodium chloride as isotonicity agent.

The formulations may be presented in unit-dose or multi-dose containers, for example sealed ampoules and vials, or may be stored in a frozen or freeze-dried (lyophilized) condition requiring only the addition of sterile liquid carrier immediately prior to use.

Preferably, the formulation is supplied as sterile suspension in a buffered physiological saline (0.9% w/v sodium chloride) aqueous solution in single-use vials.

According to a preferred embodiment of the invention, the formulation comprises poractant alfa in a concentration between 40 and 80 mg/ml, preferably 80 mg/ml.

The administration of the claimed combination may be carried out in a known manner, e.g. by endotracheal instillation, spray administration, or nebulisation by jet ultrasonic, or mesh-vibrating nebulisers commonly available on the market.

Preferably, the claimed combination is administered endotracheally.

It has indeed been found that CuZn superoxide dismutase and catalase, when administered by this route at these dosages, do not down-regulate mRNA transcription of the endogenous antioxidant enzymes.

When the combination is administered by endotracheal instillation, depending on the severity of the respiratory distress syndrome, different methods can be appropriate. For example the claimed formulation may be administered by endotracheal instillation to pre-term infants kept under continuous or intermittent positive pressure ventilation.

Alternatively, the combination may be administered in conjunction with non-invasive pulmonary respiratory therapy involving the administration of positive airway pressure. The term "non-invasive pulmonary respiratory therapy" refers to respiratory therapy which does not use mechanical ventilation and can include continuous positive airway pressure (CPAP), bilevel positive airway pressure (BiPAP), synchronized intermittent mandatory ventilation (SIMV), and the like according to methods and by using devices known to the skilled person.

In a particular embodiment, the administration can occur as described in WO 2008/148469 (which is incorporated herein by reference in its entirety), i.e. by the use of a thin catheter placed in the trachea and the patient respiration supported through specially designed nasal devices such as masks, prongs or tubes according to methodology known as nasal Continuous Positive Airway Pressure (nCPAP).

Other methods of delivery include lavage, lung wash, and the like, according to procedures known to the skilled person.

The volume of the aqueous solution in which the combined active components are suspended will depend on the desired concentration.

Advantageously, the volume of the formulation should be not more than 5.0 ml, preferably from 4.5 to 2.0 ml, more preferably from 3.5 to 2.5 ml.

Alternatively, when the exogenous pulmonary surfactant and the two antioxidant enzymes are administered separately, each individual active component may be formulated separately. In this case, the individual active components do not unconditionally have to be taken at the same time.

In the case of a separate administration, the formulation of each individual active component may be packed at the same time in a suitable container to form a kit.

Therefore, this invention also concerns a kit comprising: a) an exogenous pulmonary surfactant and a pharmaceutically acceptable carrier or diluent in a first unit dosage form; b) CuZn superoxide dismutase at a unit dose of from 2000 to 10000 U/kg, and optionally a pharmaceutically acceptable carrier or diluent in a second unit dosage form; c) catalase at a unit dose of from 2000 to 4000 U/kg, and optionally a pharmaceutically acceptable carrier or diluent in a third unit dosage form; d) container means for containing said first, second and third dosage forms.

Suitable container means include, plastic or glass vials, plastic bags or pouches, and foil pouches.

According to a particular aspect, superoxide dismutase and catalase may be present in a unique dosage form, with optionally a pharmaceutically acceptable carrier or diluent.

Preferably the first unit dosage form is a single-use vial filled with 2.5 ml of a sterile formulation of 80 mg/ml poractant alfa suspended in a buffered physiological saline (0.9% w/v sodium chloride) aqueous solution.

The combination of the invention which may be administered to the infant after the birth according to conditions which shall be established by the skilled practitioner, is suitable to prevent, delay, alleviate, arrest, inhibit, or reduce the risk of the development of bronchopulmonary dysplasia.

A suitable posology of the combination of the invention (dosages, frequency of administration) will be dependent on the patient's age and severity of the disorder and will be readily ascertainable by the attending clinician.

The frequency of dosing may vary, but typically is once every 2 to 3 days. In other embodiments, the patient is dosed more frequently, e.g., every 6 to 8 hours, twice daily, or once daily, or less frequently, e.g., twice weekly or even once weekly. In other embodiments, the patient can be dosed more frequently early in the treatment regimen, and with decreasing frequency later in the treatment regimen, e.g., once every other day for one week, followed by twice weekly until the end of the treatment period. Depending on the dosage form, e.g., aerosol or dry powder as compared with liquid suspension, the patient can be dosed continuously for part or all of the treatment period.

Preferably, the combination of the invention is suitable to prevent the development of bronchopulmonary dysplasia in pre-term infants affected by a severe form of respiratory distress syndrome (RDS).

However, it might be also used for the prophylaxis and/or treatment of other diseases related to the lack or dysfunction of the endogenous surfactant such as respiratory distress syndrome in adults (ARDS), acute lung injury (ALI), and meconium aspiration syndrome (MAS).

Other features of the invention will become apparent in the course of the following descriptions of exemplary embodiments which are given for illustration of the invention and are not intended to be limiting thereof.

EXAMPLES

Example 1

In vitro Evaluation of the Scavenger Activity of Modified Natural Surfactants After Addition of CuZn Superoxide Dismutase, Catalase, or Both The aim of this "in vitro" study was to assess the change of scavenger activity versus $H_2O_2$ of modified natural pulmonary surfactants after the addition of different amount of human CuZn superoxide dismutase, human catalase, or both. Four modified natural commercially available pulmonary surfactants were utilised:

Infasurf® (Calfactant; ONY, Inc. Amherst, N.Y., USA) is a calf lung surfactant extract containing 35 mg/ml of phospholipids;

Curosurf® (Poractant; Chiesi SpA., Parma, Italy) is a lipid extract from whole minced porcine lung tissue containing 80 mg/ml of phospholipids.

Survanta® (Beractant; Abbott Laboratories, Abbott Park, Ill., USA) is prepared from minced bovine lung extract with added dipalmitoyl phosphatidylcholine, triacylglycerol and palmitic acid. It contains 45 mg/ml of phospholipids.

Alveofact® (Bovactant; Boehringer Ingelheim Pharma, Ingelheim, Germany) is produced by lipid extraction from bovine lung lavage, and contains 45 mg/ml of phospholipids.

Human erythrocyte Cu/Zn superoxide dismutase (hereinafter SOD) and human erythrocyte catalase (hereinafter CAT) were purchased from Sigma Chemical Co., St. Louis, Mo., USA. The dose of SOD is expressed in mg. The utilised SOD had a specific activity of 2500 to 6000 U per mg of protein (enzyme).

SOD and CAT activity was measured in the selected natural surfactants. SOD activity was measured using the Superoxide Dismutase Assay Kit® (Cayman Chemical, Ann Arbor, Mich., USA), according to the manufacturer's instructions. The assay uses a tetrazolium salt for detection of superoxide radicals generated by xanthine oxidase and hypoxanthine. SOD activity was assessed by measuring the dismutation of generated superoxide radicals in a 96 well plate with a plate reader with a 450 nm filter. One unit of SOD is defined as the amount of enzyme needed to inhibit 50% dismutation of the superoxide radical. SOD activity was expressed as U/mg of phospholipids.

Catalase activity was determined using the Catalase Assay Kit® (Cayman Chemical, Ann Arbor, Mich., USA) which utilizes the peroxide function of CAT for determination of enzyme activity. It is based on the enzyme reaction with methanol in an optimal concentration of $H_2O_2$. The formaldehyde produced is measured spectrophotometrically with 4-amino-3-hydrazino-5-mercapto-1,2,4-triazole (Purpald; Aldrich chemical company, Milwaukee, Wis., USA) as the chromogen. The formaldehyde concentration of the samples was obtained from the standard curve. One unit of CAT activity is defined as the amount of enzyme that caused the formation of 1.0 nmol of formaldehyde per minute per milligram of protein at 25° C. The activity of CAT was recorded as nmol/min/mg of phospholipids.

To test scavenger activity versus $H_2O_2$, the same amount of phospholipids (4.72 mg=100 µmol of phospholipids) from each natural surfactant was incubated with 25, 50, 100, and 250 µM of $H_2O_2$ at 37° C. for 2 hours. Then, samples were centrifuged at 16,000×g for 45 minutes. The concentration of $H_2O_2$ was measured by monitoring the formation of the ABTS (2,2'-azinobis-3-ethylbenzothiazoline-6-sulfonic acid)) radical cation, as described by Casella et al. (*Inorg. Biochem.*, 2000, 79, 31-40, which is incorporated herein by reference in its entirety).

Furthermore, the scavenger activity of the four modified natural pulmonary surfactants after the addition of SOD or CAT was tested. In particular, the scavenging activity of 0.60 mL of Infasurf®, 0.50 mL of Curosurf®, 0.80 mL of Survanta®, and 0.44 mL of Alveofact® after the addition, respectively of 1 mg or 2 mg of SOD, and 3000 U or 30000 U of CAT was evaluated.

These samples were incubated with 100 μM of $H_2O_2$ at 37° C. for 2 hours, and then the concentration of $H_2O_2$ was measured as reported above.

Figure 2:
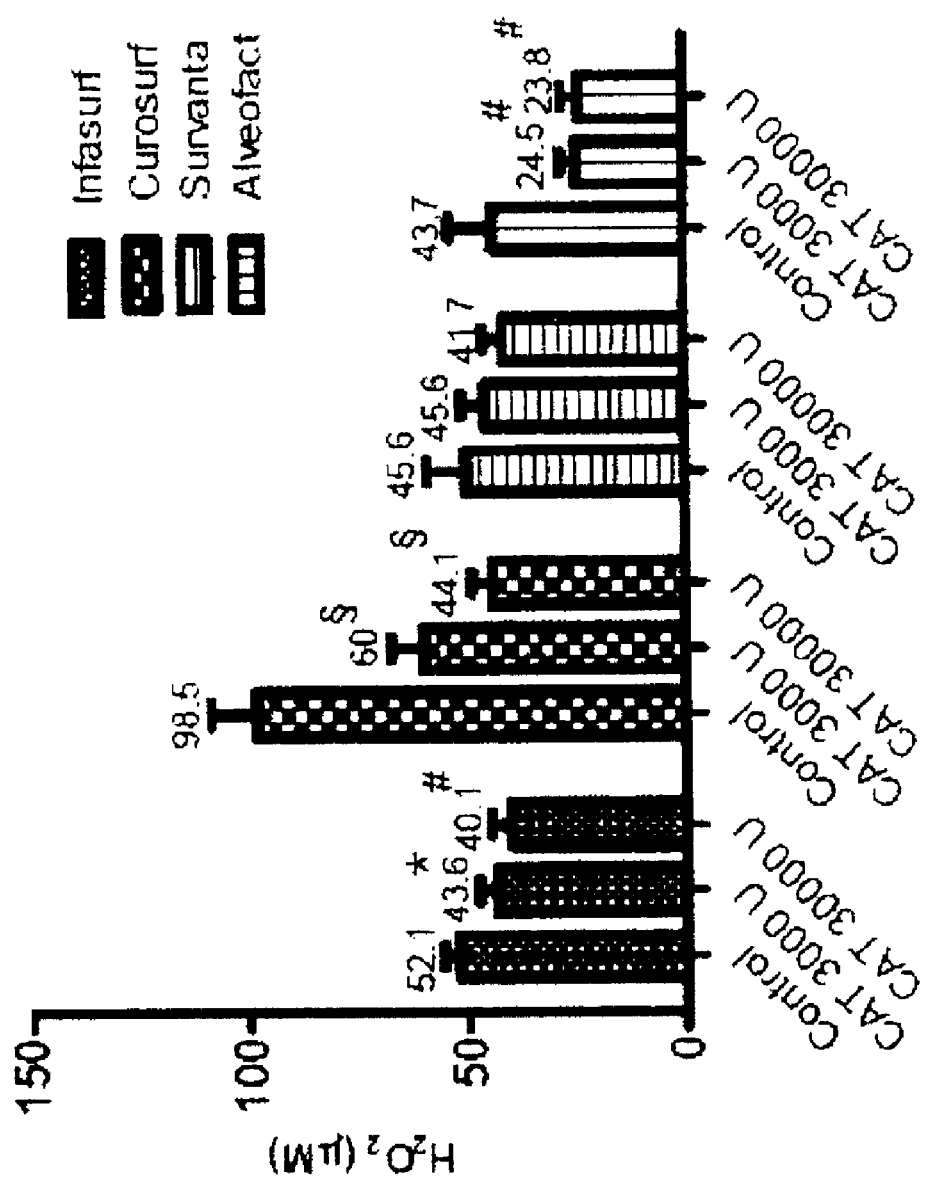
FIG. 2 shows the $H_2O_2$ concentration in the four studied modified natural pulmonary surfactants after the addition of 100 mM of $H_2O_2$ (control) and 3000 or 30000 U of catalase (CAT). Mean values and SDs. *p<0.05 vs. baseline; # p<0.005 vs. baseline; §p<0.0001 vs. baseline. Data are the difference between the time 0 and end experiment $H_2O_2$ concentration.

The results after addition of SOD are reported in FIG. 1, while the results after addition of CAT are reported in FIG. 2.

To assess the potential synergistic effect of SOD and CAT, the scavenging activity of 0.60 mL of Infasurf, 0.50 mL of Curosurf, 0.80 mL of Survanta, and 0.44 mL of Alveofact after the addition of 1 mg of SOD and 3000 units of CAT was evaluated. The results are reported in FIG. 3.

Collected data were expressed as means and standard deviations. The data were analyzed for statistically significant differences by ANOVA test within the groups and by Student's "t" test between the groups. A $p<0.05$ was considered statistically significant. From FIG. 1, it can be appreciated that the addition of SOD to surfactants is followed as expected by the increase of scavenger activity of Curosurf®, Survanta®, and Alveofact®. However, the scavenger activity does not significantly vary passing from 1 to 2 mg of SOD.

Surprisingly, the scavenger activity of Infasurf decreases. Without being limited by the theory, we speculate that this particular performance of Infasurf® might be explained by the fact that the over-expression of SOD may lead to increased oxidative stress through different mechanisms, such as an increase of $H_2O_2$ concentration, hydroxyl radical formation, and superoxide-mediated inhibition of membrane peroxidation, by acting as radical chain breaker.

From FIG. 2, after the addition of CAT, it has been observed the expected increase of scavenger activity of Infasurf®, Curosurf®, Alveofact®, and Survanta®, although the increase of this latter did not reach statistical significance. However, also in this case, the scavenger activity does not significantly vary passing from 3000 to 30000 U of CAT.

Figure 3:
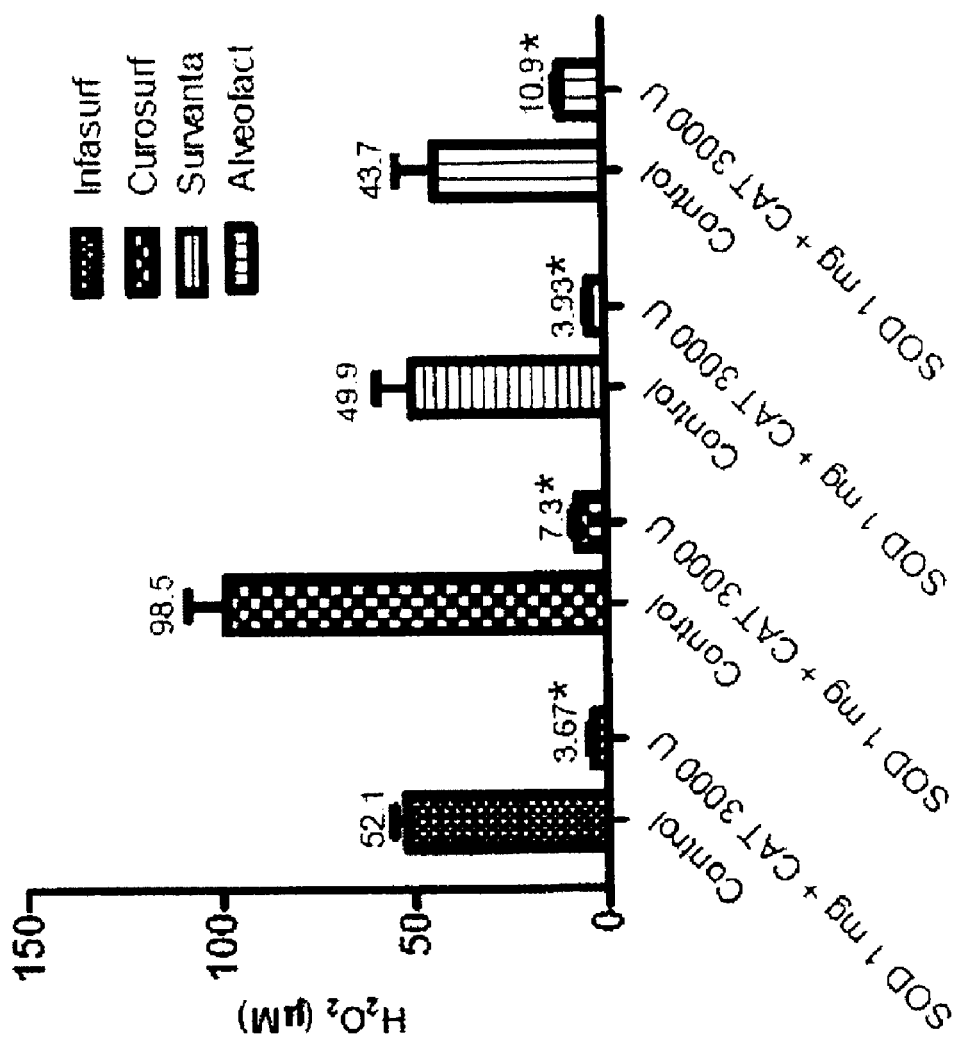
FIG. 3 shows the $H_2O_2$ concentration in the four studied modified natural pulmonary surfactants after the addition of 100 mM of $H_2O_2$ (control) and 1 mg of SOD and 3000 U of CAT. Mean values and SDs. *p<0.0001 vs. baseline. Data are the difference between the time 0 and end experiment $H_2O_2$ concentration.

Finally, from FIG. 3, it can be appreciated that, when both SOD and CAT are added to the surfactants, a very significant increase of scavenger activity against $H_2O_2$ in all the studied surfactant is observed. Moreover, this increase appears to be higher than that observed after the single addition of SOD and CAT, indicating that their action is synergic.

Example 2

In vivo Evaluation of CUROSURF® Combined with CuZn Superoxide Dismutase and Catalase An in vivo study is carried to evaluate the lung tissue oxidative stress in preterm lambs with RDS treated with the modified natural pulmonary surfactant Curosurr after the addition of SOD and CAT.

To study oxidative stress of lung tissues, total hydroperoxides (TH), advanced oxidative protein products (AOPP), isoprostane ($F_2$-IP), and non-transferrin bound iron (NTBI) are determined in the bronchial aspirate fluid (BAL).

12 preterm lambs (gestational age 126±3 days) with RDS are studied. They are intubated immediately after delivery. Initial ventilator setting is the following: $FiO_2$ 100%, RR 60/min, PIP 16-18 $cmH_2O$, PEEP 4 cm $H_2O$. Then, mechanical ventilation is adjusted for maintaining pH>7.20, $pCO_2$ 35-65 torr, $pO_2$ 55-80 torr, $SaO_2$ 85-95%). The animals are instrumented and randomized to receive natural exogenous surfactant (Curosurr, Chiesi, Parma, Italy: 200 mg/kg) or the same amount of surfactant combined with SOD (1 mg/kg) and CAT (3000 U/kg).

The study period is 6 hours. Changes of pH, $pCO_2$, $pO_2$, $SaO_2$ and BE, ventilator setting, lung mechanics (tidal volume, dynamic compliance, airway resistance), mean systemic and pulmonary pressure are recorded at preplanned intervals.

To study oxidative stress of lung tissues, total hydroperoxides (TH), advanced oxidative protein products (AOPP), isoprostane ($F_2$-IP), and non-transferrin bound iron (NTBI) are dosed in the bronchial aspirate fluid. TH is measured with a d-ROMs Kit (Diacron srl, Italy) by using the spectrophotometric procedure reported in Buonocore G et al., *Pediatr. Res.*, 2000, 47, 221-224, which is incorporated herein by reference in its entirety.

The results are expressed in conventional units, (Carr units: the value of 1 Carr unit is equal to a concentration of 0.08 mg/dL of hydrogen peroxide). AOPP is measured by the method reported in Witko-Sarsat V et al. *Kidney Int.*, 1996, 49, 1304-1313 (which is incorporated herein by reference in its entirety), using spectrophotometry on a microplate reader. The AOPP concentration is expressed as μmol/L chloramine-T equivalents. NTBI levels are determined by HPLC using the method described by Kime et al Clin Sci 1996, 91, 633-638, partially modified. $F_2$-IP are assessed in BAL after addition of butylated hydroxytoluene (BHT) to prevent oxidation during processing, as previously described in Grosso S et al., *Brain Dev.*, 2008, 30, 391-395, which is incorporated herein by reference in its entirety.

$F_2$-IP is determined in a single matrix. Ethanol is added to remove precipitated protein and acetate buffer added up to pH 4.0 for 15-$F_{2t}$-IsoP determination. Samples are purified from the metabolite with $C_{18}$ and silica Sep-Paks cartridges (Waters Co., Milford, Mass.) before using a colorimetric enzyme immunoassay (Cayman Chemical, Ann Arbor, Mich.). The antibody is highly specific for 15-$F_{2t}$-IsoP (8-Iso $PGF_2$). The range of the standard curve is from 3.9 to 500 pg/ml and the detection limit is 2 pg/ml.

Bronchial aspirate samples from animals are obtained with the following technique: 1 mL/kg sterile 0.9% saline is instilled using a 10 mL syringe through a 8F gauge feeding catheter placed in the endotracheal tube so that the tip extends 1 cm beyond the distal end of the tube. The saline is instilled and immediately aspirated back into the syringe.

All samples are clarified by centrifugation (1000 rpm×5 min), and the supernatants are immediately frozen at −70° C. and stored for subsequent analysis. Bronchial aspirate samples are obtained from each animal before and at 1, 2, 4, and 6 hours after surfactant administration.

The animals are killed with an overdose of pentobarbital. After death, the thorax is carefully opened and the trachea and lungs are removed and put in a buffered 10% formalin bath for 24 hours. Two random pulmonary specimens are obtained from the upper and the lower lobes of both lungs. Routine techniques are used to prepare the tissues for paraffin embedding. Five-micrometer thick sections are stained with hematoxylin-eosin and the microscopic examination is carried out in blind by two pathologists.

Collected data are analyzed and expressed as means and standard deviations. The data are analyzed for statistically significant differences by ANOVA test within the groups and by Student's "t" test between the groups. A $p<0.05$ are considered statistically significant.

The results confirm the synergic interaction of the combination surfactant with catalase at the tested doses.

Where a numerical limit or range is stated herein, the endpoints are included. Also, all values and subranges within a numerical limit or range are specifically included as if explicitly written out.

Obviously, numerous modifications and variations of the present invention are possible in light of the above teachings.

It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for reducing pulmonary oxidative damage, comprising administering an effective amount of a pharmaceutical composition comprising a modified natural pulmonary surfactant selected from the group consisting of poractant alfa, calfactant, bovactant, and beractant in combination with CuZn superoxide dismutase at a unit dose of from 2000 to 10000 U/kg and catalase at a unit dose of from 2000 to 4000 U/kg, to a subject in need thereof.

2. A method according to claim 1, wherein said surfactant is poractant alfa.

3. A method according to claim 2, wherein poractant alfa is present in an amount of from 100 to 200 mg/kg.

4. A method according to claim 1, wherein the unit dose of CuZn superoxide dismutase is from 2500 to 6000 U/kg.

5. A method according to claim 1, wherein the unit dose of catalase is from 2500 to 3500 U/kg.

6. A method for reducing the risk of developing bronchopulmonary dysplasia, comprising administering an effective amount of a pharmaceutical composition comprising a modified natural pulmonary surfactant selected from the group consisting of poractant alfa, calfactant, bovactant, and beractant in combination with CuZn superoxide dismutase at a unit dose of from 2000 to 10000 U/kg and catalase at a unit dose of from 2000 to 4000 U/kg, to a subject in need thereof.

7. A method according to claim 6, wherein said surfactant is poractant alfa.

8. A method according to claim 7, wherein poractant alfa is present in an amount of from 100 to 200 mg/kg.

9. A method according to claim 8, wherein the unit dose of CuZn superoxide dismutase is from 2500 to 6000 U/kg.

10. A method according to claim 6, wherein the unit dose of catalase is from 2500 to 3500 U/kg.

11. A method according to claim 6, wherein said subject is a preterm infant.

* * * * *